(12) United States Patent
Yang et al.

(10) Patent No.: US 9,102,583 B2
(45) Date of Patent: *Aug. 11, 2015

(54) METHOD FOR PRODUCING ETHYLENE GLYCOL FROM OXALATE THROUGH THE FLUIDIZED BED CATALYTIC REACTION

(75) Inventors: Weimin Yang, Shanghai (CN); Juntao Liu, Shanghai (CN); Wanmin Wang, Shanghai (CN); Jun Kuai, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/000,876

(22) PCT Filed: Feb. 24, 2012

(86) PCT No.: PCT/CN2012/000236
§ 371 (c)(1),
(2), (4) Date: Aug. 22, 2013

(87) PCT Pub. No.: WO2012/113267
PCT Pub. Date: Aug. 30, 2012

(65) Prior Publication Data
US 2013/0331617 A1    Dec. 12, 2013

(30) Foreign Application Priority Data

Feb. 25, 2011 (CN) ............ 2011 1 0045356
Feb. 25, 2011 (CN) ............ 2011 1 0045364

(51) Int. Cl.
| | | |
|---|---|---|
| *C07C 27/04* | (2006.01) | |
| *C07C 29/149* | (2006.01) | |
| *B01J 23/83* | (2006.01) | |
| *B01J 23/84* | (2006.01) | |
| *B01J 23/843* | (2006.01) | |
| *B01J 23/888* | (2006.01) | |
| *B01J 29/48* | (2006.01) | |

(52) U.S. Cl.
CPC ............ *C07C 29/149* (2013.01); *B01J 23/83* (2013.01); *B01J 23/84* (2013.01); *B01J 23/8437* (2013.01); *B01J 23/888* (2013.01); *B01J 29/48* (2013.01)

(58) Field of Classification Search
CPC ...... C07C 29/149; C07C 31/202; B01J 23/83; B01J 23/84; B01J 23/8437; B01J 23/888; B01J 29/48
USPC ........................................ 568/864
See application file for complete search history.

(56) References Cited

U.S. PATENT DOCUMENTS

| | | | |
|---|---|---|---|
| 4,112,245 A | * | 9/1978 | Zehner et al. ............ 568/864 |
| 4,440,873 A | | 4/1984 | Miyazaki et al. |
| 4,649,226 A | | 3/1987 | Poppelsdorf et al. |
| 2007/0142648 A1 | | 6/2007 | Urtel et al. |

FOREIGN PATENT DOCUMENTS

| | | | |
|---|---|---|---|
| CN | 1918095 A | | 2/2007 |
| CN | 101138725 A | | 3/2008 |
| CN | 101475443 A | | 7/2009 |
| CN | 101474561 | * | 8/2009 |
| CN | 101879448 | * | 11/2010 |
| CN | 102219640 | * | 10/2011 |
| WO | 2006/137165 A1 | | 12/2006 |
| WO | WO2012113268 | * | 8/2012 |

OTHER PUBLICATIONS

CN101474561 description translation 2009.*
CN101474561 claims translation 2009.*
CN102219640 description translation 2011.*
CN102219640 claims translation 2011.*
WO2012113268 description translation 2012.*
CN101879448 description translation 2010.*
CN101879448 claims translation 2010.*
Zhang, Qiyun et al. "Hydrogenation of Dimethyl Oxalate to Ethylene Glycol", Petrochemical Technology, 2007, vol. 36, No. 4, pp. 340-344.
Li, Zhuxia et al. "Studies on Hydrogenation of Dimethyl Oxalate on Cu/SiO2 Catalyst", Chemical Reaction Engineering and Technology. Jun. 2004 vol. 20, No. 2, pp. 121-128.
Huang, Dangmu et al. "Simulation Test on Catalytic Hydrogenation of Diethyl Oxalate to Ethylene Glycol", Industrial Catalysis, 1996 No. 4, pp. 24-29.
International Search Report (PCT/ISA/210) Issued on May 31, 2012, by the China Patent Office as the International Searching Authority for International Application No. PCT/CN2012/000236.

* cited by examiner

*Primary Examiner* — Yevegeny Valenrod
*Assistant Examiner* — Blaine G Doletski
(74) *Attorney, Agent, or Firm* — Buchanan Ingersoll & Rooney PC

(57) ABSTRACT

A process for producing ethylene glycol includes contacting an oxalate with a fluidized bed catalyst under the following conditions: a reaction temperature of from about 170 to about 270° C., a weight space velocity of oxalate of from about 0.2 to about 7 hours$^{-1}$, a hydrogen/ester molar ratio of about 20~200:1, a reaction pressure of from about 1.5 to about 10 MPa, and a reaction temperature difference $\Delta T$ of from about 1 to about 15° C. The fluidized bed catalyst includes: a) from about 5 to about 80 parts by weight of copper and the oxide thereof, b) from about 10 to about 90 parts by weight of at least one carrier selected from silica, molecular sieve or alumina, c) from about 0.01 to about 30 parts by weight of bismuth and tungsten metallic elements or the oxides thereof, or cerium and niobium metallic elements or the oxides thereof.

10 Claims, No Drawings

METHOD FOR PRODUCING ETHYLENE GLYCOL FROM OXALATE THROUGH THE FLUIDIZED BED CATALYTIC REACTION

TECHNICAL FIELD

The invention relates to a process for producing ethylene glycol from oxalate through a fluidized bed catalytic reaction, in particular to a process for producing ethylene glycol from dimethyl oxalate or diethyl oxalate through a fluidized bed catalytic reaction.

BACKGROUND TECHNOLOGY

Ethylene glycol (EG) is an important organic chemical raw material, which is mainly used for producing polyester fibers, antifreezes, unsaturated polyester resins, lubricants, plasticizers, non-ionic surfactants and explosives. In addition, ethylene glycol can also be used in such fields as coating, photographic developer, brake fluid and ink, as the solvent and medium of ammonium perborate and for producing special solvents like glycol ether. Ethylene glycol has a wide range of uses.

At present, China has surpassed the U.S. and become the largest ethylene glycol consumer in the world, an average annual growth rate of the domestic apparent consumption from 2001 to 2006 is 17.4%. Although the production capacity and production of ethylene glycol in China increase rapidly, due to the vigorous development of industries like polyester, they still cannot meet the growing market demand, which requires imports in large quantities every year. Moreover, the imports show growth year after year.

Currently, both domestic and foreign large industrial productions of ethylene glycol adopt the process route of direct hydration of ethylene oxide, namely pressure hydration. The production technology is basically monopolized by three companies including Royal Dutch Shell, U.S. Halcon-SD and the U.S. UCC. In addition, the research and development work of the new synthesis technology of ethylene glycol has been making progress, for example, companies such as Shell, UCC, Mendeleyev University of Chemical Technology of Russia, Shanghai Research Institute of Petrochemical Technology, etc. have successively developed a technology for producing ethylene glycol by the catalytic hydration of ethylene oxide; Halcon-SD, UCC, Dow Chemical, NsKK and MCC have successively developed a technology for producing ethylene glycol by the ethylene carbonate process; Dow Chemical and other companies have developed a technology for producing ethylene glycol by the co-production of EG and dimethyl carbonate (DMC).

As to the direct hydration, it produces the reaction products of high water content, has a long process of the subsequent devices (evaporator), huge equipment and high energy consumption, and has an overall yield of the process of only 70%, directly affects the production cost of EG. Compared with the direct hydration process, the catalytic hydration process significantly reduces the water ratio and meanwhile obtains relatively high EC conversion ratio and ethylene glycol selectivity. If the problems of the catalyst stability and the relevant engineering technical problems are solved well, it will be the trend to prepare EG by the EC catalytic hydration process instead of non-catalytic hydration process. The technology of producing ethylene glycol by the ethylene carbonate (EC) process, which has relatively large advantages over the direct hydration of EO in terms of the EC conversion ratio, the ethylene glycol selectivity, the consumption of the raw materials and energy, is a leading process. The co-production technology of ethylene glycol and DMC can make full use of the $CO_2$ resources by-produced by ethylene oxidation. In the existing EC manufacturing devices, only the addition of the reaction step for producing EC can produce two very valuable products. Said technology is very attractive.

However, the common drawback of the above processs is they need to consume ethylene resources. Under the current situation where ethylene is mainly obtained by conventionally refining the oil resources, and the global oil prices will be at a high level in the next period of time, producing ethylene glycol by using natural gas or coal that is abundant and cheap instead of oil (non-oil route, also referred to as CO route) has advantages of being able to compete with the conventional ethylene route. Among them, the new technology of synthesizing EG by synthesis gas may exert significant impact on the innovation of the EG production process. It is a very attractive coal chemical industry route to prepare dimethyl oxalate with carbon monoxide as the raw material and then prepare ethylene glycol by hydrogenating dimethyl oxalate. Nowadays, both domestic and foreign studies in preparing dimethyl oxalate with carbon monoxide as the raw material have achieved excellent effects, and the industrial production has been mature. However, as regards the preparation of ethylene glycol by the hydrogenation of dimethyl oxalate, there is still much research work to be required, especially, there is no good breakthrough regarding how to effectively improve the selectively for ethylene glycol and enhance the stability of the catalyst.

Document CN101138725A discloses a catalyst for synthesizing ethylene glycol by the hydrogenation of the oxalic ester and a process for preparing the same, the catalyst uses the copper metal as the active component, and zinc as the promoter, and is manufactured with the coprecipitation process. However, said catalyst leads to low conversion ratio of oxalic ester. Meanwhile, there is no report on the stability of the catalyst.

Document "Petrochemical Technology", 2007, vol. 36, No. 4, p340–343 describes a study on the reaction of synthesizing ethylene glycol by hydrogenation of dimethyl oxalate using $Cu/SiO_2$. However, said catalyst has poor selectivity, and there is no report on the stability of the catalyst.

SUMMARY OF THE INVENTION

The technical problem to be solved in the present invention is to solve the problem of low selectivity for the hydrogenation product ethylene glycol present in the prior art, and to provides a novel process for producing ethylene glycol from oxalate through the fluidized bed catalytic reaction. Said process has the advantage of high selectivity for the hydrogenation product ethylene glycol.

To solve the above technical problem, the present invention adopts the following technical solution: a process for producing ethylene glycol, comprising using a fluidized bed reactor, using oxalate as the raw materials, and contacting the raw materials with the fluidized bed catalyst under the following conditions: reaction temperature being from about 170° C. to about 270° C., the space velocity of oxalate weight being from about 0.2 hours$^{-1}$ to about 7 hours$^{-1}$, the hydrogen/ester molar ratio being from about 20 to about 200:1, reaction pressure being from about 1.5 MPa to about 10 MPa, and reaction temperature difference $\Delta T$ being from about 1° C. to about 15° C., to produce an effluent containing ethylene glycol;

wherein said fluidized bed catalyst is a catalyst comprising copper and the oxide thereof;

Based on the parts by weight, said fluidized bed catalyst comprises a) from about 5 to about 80 parts of copper and the oxide thereof, b) from about 10 to about 90 parts of at least one carrier selected from silica, molecular sieve or alumina, c) from about 0.01 to about 30 parts of bismuth and tungsten metallic elements or the oxides thereof, or cerium and niobium metallic elements or the oxides thereof; wherein the average specific surface area of the carrier of the fluidized bed catalyst ranges from about 50 to about 800 $m^2/g$, the average particle diameter of the catalyst ranges from about 20 to about 300 microns, the abrasion index of the catalyst ranges from about 0.1 to about 1.5, preferably from about 0.2 to about 0.8.

The reaction conditions of the fluidized bed reactor in the above technical solution are preferably as follows: the reaction temperature ranges from about 180° C. to about 260° C.; the weight space velocity of oxalates ranges from about 0.3 $h^{-1}$ to about 3 $h^{-1}$, the hydrogen/ester molar ratio ranges from about 50 to about 150:1; the reaction pressure ranges from about 2.0 MPa to about 6.0 MPa. Oxalate is preferably selected from dimethyl oxalate, diethyl oxalate or the mixture thereof.

The advantage of using a fluidized bed reactor in the present invention lies in that when using a fluidized bed reactor, the weight space velocity of the oxalate ranges from about 0.2 to about 7 $h^1$, the reaction temperature difference $\varDelta T$ is controlled at from about 1 to about 15° C., preferably from about 1 to about 10° C., more preferably from about 1 to about 5° C. Said reaction temperature difference $\varDelta T$ represents the difference between the hot-spot temperature of the reactor catalyst and the starting temperature of the reaction between the raw material entering into the reactor and the catalyst.

In the above technical solution, based on the parts by weight, said fluidized bed catalyst preferably comprises a) from about 10 to about 60 parts of copper and the oxide thereof, b) from about 15 to about 90 parts of at least one carrier selected from silica or alumina, c) from about 0.05 to about 20 parts of bismuth and tungsten metallic elements or the oxides thereof, or cerium and niobium metallic elements or the oxides thereof. The average specific surface area of the carrier preferably is from about 50 $m^2/g$ to about 600 $m^2/g$, and the average particle diameter of the catalyst preferably ranges from about 50 microns to about 200 microns. Based on the parts by weight, more preferably the bismuth metallic element and the oxide thereof as promoter are from about 0.01 to about 20 parts, and more preferably the tungsten metallic element and the oxide thereof as promoter are from about 0.01 to about 20 parts. Based on the parts by weight, more preferably the cerium metallic element and the oxide thereof as promoter are from about 0.01 to about 20 parts, and more preferably the niobium metallic element and the oxide thereof as promoter are from about 0.01 to about 20 parts.

The catalyst in the process of the present invention is prepared by the following steps: (a) formulating a solution of the mixed nitrates of copper, bismuth and tungsten or of copper, cerium and niobium at certain concentrations and a solution of sodium carbonate at certain concentration; (b) coprecipitating the above solutions at a temperature of from about 60 to about 80° C., and constantly stirring during the precipitation process so that pH=5~8 when the precipitation is terminated; (c) repeatedly washing the above precipitated slurry with deionized water until $Na^+$ is absent, then a binder is added, and then stirring the slurry; (d) spray-forming by using the pressure spray dryer according to the desired particle size, wherein the average diameter of the catalyst particles ranges from about 20 microns to about 300 microns, preferably from about 50 microns to about 200 microns, and the particles are spherical; (e) drying for from about 4 hours to about 10 hours at about 120° C., and calcining for from about 2 hours to about 6 hours at a temperature of from about 300° C. to about 500° C.

The catalyst in the process of the present invention has the following characteristics:
1. the catalyst is formed by spray drying to obtain microspheric catalyst particles suitable for the fluidized bed;
2. the introduction of bismuth and tungsten, or of cerium and niobium as promoters into the catalyst enables the catalyst to present better catalytic performance.

In the case of using the process of the present invention and the catalyst prepared in the present invention, using a fluidized bed reactor, and using the oxalates as the raw material, under the following conditions: the reaction temperature being from about 170° C. to about 270° C., the weight space velocity of oxalate being from about 0.2 $h^{-1}$ to about 5 $h^{-1}$, the hydrogen/ester molar ratio being about 40~200:1, and the reaction pressure being from about 1.5 MPa to about 10 MPa, the conversion ratio of the oxalate is about 100%, the selectivity for ethylene glycol is greater than about 90%, the stability of the catalyst is improved, and better technical effects are obtained.

The present invention is further illustrated by the following examples and comparative examples, but the present invention is not limited to these examples.

SPECIFIC EMBODIMENTS

Example 1

The catalyst was prepared according to the contents of 20 wt % Cu+0.8 wt % Bi+2 wt % W and the balance of silica, wherein the steps were as follows: (a) formulating a solution of a mixed nitrates of copper, bismuth and tungsten and a solution of sodium carbonate; (b) coprecipitating the above solutions at about 70° C., and constantly stirring during the precipitation process so that pH=6 when the precipitation was terminated; (c) repeatedly washing the above precipitated slurry with deionized water until $Na^+$ was absent, then adding a silica carrier (with a specific surface area of 150 $m^2/g$) and a silica sol binder at concentration of 10%, and then stirring the slurry; (d) spray forming by using the pressure spray dryer to control the average diameter of the spherical catalyst particles to be 100 microns; (e) drying for 6 hours at 120° C., and calcining for 4 hours at 450° C. The fluidized bed catalyst A1 was obtained having an abrasion index of 0.2.

A fluidized bed reactor was used, and pure dimethyl oxalate (obtained from Shanghai Sinopharm, analytical pure) was used as the raw material. Under the conditions of a reaction temperature of 218° C., a weight space velocity of 0.5 $h^{-1}$, a hydrogen/ester molar ratio of 80:1, and a reaction pressure of 2.8 MPa, the raw material was contacted with the catalyst A1, and the effluent containing ethylene glycol was produced by the reaction. The resultants of the reaction were as follows:

the conversion ratio of dimethyl oxalate being 100% and the selectivity for ethylene glycol being 97.6%.

Example 2

According to the same procedure and conditions as in Example 1, except that the average diameter of the spherical catalyst particles was controlled to be 150 microns when the catalyst were formed, and the average specific surface area of the carrier was 280 $m^2/g$. The thus prepared catalyst B1 contained 30 wt % Cu+10 wt % Bi+1 wt % W and the balance of silica and had an abrasion index of 0.4. A fluidized bed reactor was used, and the methanol solution of dimethyl oxalate was used as the raw material. Under the following conditions: reaction temperature being 250° C., a weight space velocity being 6 h$^{-1}$, a hydrogen/ester molar ratio being 100:1, a reaction pressure being 3.0 MPa, and a weight percentage of dimethyl oxalate being 35% (with the balance of methane), the conversion ratio of dimethyl oxalate was 100%, and the selectivity for ethylene glycol was 95%.

Example 3

The catalyst was prepared according to the contents of 40 wt % Cu+0.8 wt % Bi+15 wt % W and the balance of silica and alumina, wherein the steps were as follows: (a) formulating a solution of a mixed nitrates of copper, bismuth and tungsten and a solution of sodium carbonate; (b) coprecipitating the above solutions at 65° C., and constantly stirring during the precipitation process so that pH=7 when the precipitation was terminated; (c) repeatedly washing the above precipitated slurry with deionized water until Na$^+$ was absent, then adding an alumina carrier (with a specific surface area of 300 m$^2$/g) and a silica sol binder at concentration of 15%, and then stirring the slurry; (d) spray-forming by using the pressure spray dryer to control the average diameter of the spherical catalyst particles to be 150 microns; (e) drying for 6 hours at 120° C., and calcining for 4 hours at 450° C. The fluidized bed catalyst C1 was obtained having an abrasion index of 0.6.

A fluidized bed reactor was used, and diethyl oxalate (obtained from Shanghai Sinopharm, analytical pure) was used as the raw material. Under the following conditions: a reaction temperature being 205° C., a weight space velocity being 0.5 h$^{-1}$, a hydrogen/ester molar ratio being 100:1, and a reaction pressure being 2.8 Mpa, the conversion ratio of diethyl oxalate was 99%, and the selectivity for ethylene glycol was 96.5%.

Example 4

The catalyst was prepared according to the contents of 30 wt % Cu+2 wt % Bi+6 wt % W and the balance of silica and alumina, wherein the steps were as follows: (a) formulating a solution of a mixed nitrates of copper, bismuth and tungsten and a solution of sodium carbonate; (b) coprecipitating the above solutions at 65° C., and constantly stirring during the precipitation process so that pH=7 when the precipitation was terminated; (c) repeatedly washing the above precipitated slurry with deionized water until Na$^+$ was absent, then adding an alumina carrier (with a specific surface area of 100 m$^2$/g) and a silica sol binder at concentration of 6%, and then stirring the slurry; (d) spray forming by using the pressure spray dryer to control the average diameter of the spherical catalyst particles to be 120 microns; (e) drying for 6 hours at 120° C., and calcining for 4 hours at 450° C. The fluidized bed catalyst D1 was obtained having an abrasion index of 1.2.

A fluidized bed reactor was used, and diethyl oxalate (obtained from Shanghai Sinopharm, analytical pure) was used as the raw material. Under the following conditions: a reaction temperature being 235° C., a weight space velocity being 4 h$^{-1}$, a hydrogen/ester molar ratio being 60:1, and a reaction pressure being 3.8 Mpa, the conversion ratio of diethyl oxalate was 99%, and the selectivity for ethylene glycol was 94.8%.

Example 5

The catalyst was prepared according to the contents of 45 wt % Cu+8 wt % Bi+2 wt % W and the balance of ZSM-5 molecular sieve, wherein the steps were as follows: (a) formulating a solution of a mixed nitrates of copper, bismuth and tungsten and a solution of sodium carbonate; (b) coprecipitating the above solutions at 65° C., and constantly stirring during the precipitation process so that pH=5 when the precipitation was terminated; (c) repeatedly washing the above precipitated slurry with deionized water until Na$^+$ was absent, then adding an ZSM-5 molecular sieve carrier (with a specific surface area of 450 m$^2$/g), and then stirring the slurry; (d) spray forming by using the pressure spray dryer to control the average diameter of the spherical catalyst particles to be 140 microns; (e) drying for 6 hours at 120° C., and calcining for 4 hours at 450° C. The fluidized bed catalyst E1 was obtained having an abrasion index of 0.3.

A fluidized bed reactor was used, and dimethyl oxalate (obtained from Shanghai Sinopharm, analytical pure) was used as the raw material. Under the following conditions: a reaction temperature being 230° C., a weight space velocity being 0.3 h$^{-1}$, a hydrogen/ester molar ratio being 70:1, and a reaction pressure being 2.2 Mpa, the conversion ratio of dimethyl oxalate was 100%, and the selectivity for ethylene glycol was 95%.

Example 6

The catalyst was prepared according to the contents of 25 wt % Cu+0.8 wt % Bi+4 wt % W and the balance of ZSM-5 molecular sieve, wherein the steps were as follows: (a) formulating a solution of a mixed nitrates of copper, bismuth and tungsten and a solution of sodium carbonate; (b) coprecipitating the above solutions at 65° C., and constantly stirring during the precipitation process so that pH=5 when the precipitation was terminated; (c) repeatedly washing the above precipitated slurry with deionized water until Na$^+$ was absent, then adding an ZSM-5 molecular sieve carrier (with a specific surface area of 400 m$^2$/g), and then stirring the slurry; (d) spray forming by using the pressure spray dryer to control the average diameter of the spherical catalyst particles to be 140 microns; (e) drying for 6 hours at 120° C., and calcining for 4 hours at 450° C. The fluidized bed catalyst F1 was obtained having an abrasion index of 0.7.

A fluidized bed reactor was used, and dimethyl oxalate (obtained from Shanghai Sinopharm, analytical pure) was used as the raw material. Under the following conditions: a reaction temperature being 230° C., a weight space velocity being 0.2 h$^{-1}$, a hydrogen/ester molar ratio being 100:1, a reaction pressure being 2.8 MPa, and a weight percentage of dimethyl oxalate being 14.5%. The conversion ratio of dimethyl oxalate was 100%, and the selectivity for ethylene glycol was 98%.

Example 7

The catalyst was prepared according to the contents of 20 wt % Cu+5 wt % Ce+2 wt % Nb and the balance of silica, wherein the steps were as follows: (a) formulating a solution of a mixed nitrates of copper, cerium and niobium and a solution of sodium carbonate; (b) coprecipitating the above solutions at 70° C., and constantly stirring during the precipitation process so that pH=6 when the precipitation was terminated; (c) repeatedly washing the above precipitated slurry with deionized water until Na$^+$ was absent, then adding a silica carrier (with a specific surface area of 150 m$^2$/g) and a silica sol binder at concentration of 10%, and then stirring the slurry; (d) spray forming by using the pressure spray dryer to control the average diameter of the spherical catalyst particles to be 100 microns; (e) drying for 6 hours at 120° C., and calcining for 4 hours at 450° C. The fluidized bed catalyst A2 was obtained having an abrasion index of 0.4.

A fluidized bed reactor was used, and dimethyl oxalate (obtained from Shanghai Sinopharm, analytical pure) was used as the raw material. Under the conditions of a reaction temperature being 220° C., a weight space velocity being 0.5 $h^{-1}$, a hydrogen/ester molar ratio being 80:1, and a reaction pressure being 2.8 Mpa, the raw material was contacted with catalyst A2, and the effluent containing ethylene glycol was produced by the reaction. The resultants of the reaction were as follows: the conversion ratio of dimethyl oxalate being 100%, and the selectivity for ethylene glycol being 92%.

Example 8

The same procedure and conditions as in Example 7 were used, except that the average diameter of the spherical catalyst particles was controlled to be 150 microns when the catalyst was formed, and the average specific surface area of the carrier was 280 $m^2/g$. The thus prepared catalyst B2 contained 30 wt % Cu+10 wt % Ce+1 wt % Nb and the balance of silica and had an abrasion index of 0.5. A fluidized bed reactor was used, and the solution of dimethyl oxalate in methanol was used as the raw material. Under the following conditions: a reaction temperature being 250° C., a weight space velocity being 6 $h^{-1}$, a hydrogen/ester molar ratio being 100:1, a reaction pressure being 3.0 MPa, and a weight percentage of dimethyl oxalate being 35% (with the balance of methane), the conversion ratio of dimethyl oxalate was 100%, and the selectivity for ethylene glycol was 95%.

Example 9

The catalyst was prepared according to the contents of 40 wt % Cu+1.5 wt % Ce+15 wt % Nb and the balance of silica and alumina, wherein the steps were as follows: (a) formulating a solution of a mixed nitrates of copper, cerium and niobium and a solution of sodium carbonate; (b) coprecipitating the above solutions at 65° C., and constantly stirring during the precipitation process so that pH=7 when the precipitation was terminated; (c) repeatedly washing the above precipitated slurry with deionized water until Na$^+$ was absent, then adding an alumina carrier (with a specific surface area of 300 $m^2/g$) and a silica sol binder at concentration of 15%, and then stirring the slurry; (d) spray forming by using the pressure spray dryer to control the average diameter of the spherical catalyst particles to be 150 microns; (e) drying for 6 hours at 120° C., and calcining for 4 hours at 450° C. The fluidized bed catalyst C2 was obtained having an abrasion index of 0.4.

A fluidized bed reactor was used, and diethyl oxalate (obtained from Shanghai Sinopharm, analytical pure) was used as the raw material. Under the following conditions: a reaction temperature being 203° C., a weight space velocity being 0.5 $h^{-1}$, a hydrogen/ester molar ratio being 100:1, and a reaction pressure being 2.8 Mpa, the conversion ratio of diethyl oxalate was 99%, and the selectivity for ethylene glycol was 97.3%.

Example 10

The catalyst was prepared according to the contents of 30 wt % Cu+1 wt % Ce+8 wt % Nb and the balance of silica and alumina, wherein the steps were as follows: (a) formulating a solution of a mixed nitrates of copper, cerium and niobium and a solution of sodium carbonate; (b) coprecipitating the above solutions at 65° C., and constantly stirring during the precipitation process so that pH=7 when the precipitation was terminated; (c) repeatedly washing the above precipitated slurry with deionized water until Na$^+$ was absent, then adding an alumina carrier (with a specific surface area of 100 $m^2/g$) and a silica sol binder at concentration of 6%, and then stirring the slurry; (d) spray forming by using the pressure spray dryer to control the average diameter of the spherical catalyst particles to be 120 microns; (e) drying for 6 hours at 120° C., and calcining for 4 hours at 450° C. The fluidized bed catalyst D2 was obtained having an abrasion index of 0.2.

A fluidized bed reactor was used, and diethyl oxalate (obtained from Shanghai Sinopharm, analytical pure) was used as the raw material. Under the following conditions: a reaction temperature being 230° C., a weight space velocity being 4 $h^{-1}$, a hydrogen/ester molar ratio being 60:1, and a reaction pressure being 3.8 Mpa, the conversion ratio of diethyl oxalate was 99%, and the selectivity for ethylene glycol was 95.8%.

Example 11

The catalyst was prepared according to the contents of 45 wt % Cu+8 wt % Ce+2 wt % Nb and the balance of ZSM-5 molecular sieve, wherein the steps were as follows: (a) formulating a solution of a mixed nitrates of copper, cerium and niobium and a solution of sodium carbonate; (b) coprecipitating the above solutions at 65° C., and constantly stirring during the precipitation process so that pH=5 when the precipitation was terminated; (c) repeatedly washing the above precipitated slurry with deionized water until Na$^+$ was absent, then adding a ZSM-5 molecular sieve carrier (with a specific surface area of 450 $m^2/g$), and then stirring the slurry; (d) spray forming by using the pressure spray dryer to control the average diameter of the spherical catalyst particles to be 140 microns; (e) drying for 6 hours at 120° C., and calcining for 4 hours at 450° C. The fluidized bed catalyst E2 was obtained having an abrasion index of 0.3.

A fluidized bed reactor was used, and dimethyl oxalate (obtained from Shanghai Sinopharm, analytical pure) was used as the raw material. Under the following conditions: a reaction temperature being 230° C., a weight space velocity being 0.3 $h^{-1}$, a hydrogen/ester molar ratio being 70:1, and a reaction pressure being 2.2 Mpa, the conversion ratio of dimethyl oxalate was 100%, and the selectivity for ethylene glycol was 95%.

Example 12

The catalyst was prepared according to the contents of 25 wt % Cu+0.8 wt % Ce+4 wt % Nb and the balance of ZSM-5 molecular sieve, wherein the steps were as follows: (a) formulating a solution of a mixed nitrates of copper, cerium and niobium and a solution of sodium carbonate; (b) coprecipitating the above solutions at 65° C., and constantly stirring during the precipitation process so that pH=5 when the precipitation was terminated; (c) repeatedly washing the above precipitated slurry with deionized water until Na$^+$ was absent, then adding a ZSM-5 molecular sieve carrier (with a specific surface area of 400 $m^2/g$), and then stirring the slurry; (d) spray forming by using the pressure spray dryer to control the average diameter of the spherical catalyst particles to be 140 microns; (e) drying for 6 hours at 120° C., and calcining for 4 hours at 450° C. The fluidized bed catalyst F2 was obtained having an abrasion index of 0.1.

A fluidized bed reactor was used, and the solution of dimethyl oxalate (obtained from Shanghai Sinopharm, analytical pure) in methanol was used as the raw material. Under the following conditions: a reaction temperature being 230° C., a weight space velocity being 0.2 h$^{-1}$, a hydrogen/ester molar ratio being 100:1, a reaction pressure being 2.8 MPa, and a weight percentage of dimethyl oxalate being 14.5%, the conversion ratio of dimethyl oxalate was 100%, and the selectivity for ethylene glycol was 98%.

Comparative Example 1

The catalyst according to the document U.S. Pat. No. 4,440,873 was adopted. According to the procedure and conditions in Example 6, the results of the reaction were: the conversion ratio of dimethyl oxalate being 99%, and the selectivity for ethylene glycol being 95%.

Comparative Example 2

The same catalyst and reaction conditions as in Example 2 were adopted, except that the reaction was carried out in a fixed bed reactor. The conversion ratio of dimethyl oxalate was 100%; and the selectivity for ethylene glycol was 87%.

Comparative Example 3

The same catalyst, reaction conditions and raw material as in Example 10 were adopted, except that the reaction was carried out in a fixed bed reactor. The conversion ratio of diethyl oxalate was 99%; and the selectivity for ethylene glycol being 88%.

What is claimed is:

1. A process for producing ethylene glycol, the process comprising contacting an oxalate as a raw material with a fluidized bed catalyst under the following conditions:
   a reaction temperature of from about 170° C. to about 270° C., a weight space velocity of the oxalate of from about 0.2 h$^{-1}$ to about 7 h$^{-1}$, a hydrogen/ester molar ratio of from about 20:1 to about 200:1, a reaction pressure of from about 1.5 MPa to about 10 MPa, and a reaction temperature difference $\varDelta$T of from about 1° C. to about 15° C., to produce an effluent containing ethylene glycol;
   wherein said fluidized bed catalyst comprises: a) from about 5 to about 80 parts by weight of copper and an oxide thereof, b) from about 10 to about 90 parts by weight of at least one carrier selected from the group consisting of silica, molecular sieve and alumina, c) from about 0.01 to about 30 parts by weight of bismuth and tungsten metallic elements or the oxides thereof, or cerium and niobium metallic elements or the oxides thereof.

2. The process for producing ethylene glycol according to claim 1, wherein the fluidized bed reaction temperature ranges from about 180° C. to about 260° C., the weight space velocity of the oxalates ranges from about 0.3 h$^{-1}$ to about 3 h$^{-1}$, the hydrogen/ester molar ratio ranges from about 50:1 to about 150:1 and the reaction pressure ranges from about 2.0 MPa to about 6.0 MPa.

3. The process for producing ethylene glycol according to claim 1, wherein an average specific surface area of a carrier of the fluidized bed catalyst ranges from about 50 m$^2$/g to about 800 m$^2$/g.

4. The process for producing ethylene glycol according to claim 1, wherein an average particle diameter of the fluidized bed catalyst ranges from about 20 microns to about 300 microns, and an abrasion index of the fluidized bed catalyst ranges from about 0.1 to about 1.5.

5. The process for producing ethylene glycol according to claim 1, wherein when the weight space velocity of the oxalate ranges from about 0.2 h$^{-1}$ to about 7 h$^{-1}$, the reaction temperature difference $\varDelta$T ranges from about 1° C. to about 10° C.

6. The process for producing ethylene glycol according to claim 1, wherein said fluidized bed catalyst comprises: a) from about 10 to about 60 parts by weight of copper and an oxide thereof, b) from about 15 to about 90 parts by weight of at least one carrier selected from the group consisting of silica and alumina, c) from about 0.05 to about 20 parts by weight of bismuth and tungsten metallic elements or oxides thereof, or cerium and niobium metallic elements or oxides thereof.

7. The process for producing ethylene glycol according to claim 1, wherein an average specific surface area of a carrier of the fluidized bed catalyst ranges from about 50 m$^2$/g to about 600 m$^2$/g, and an average particle diameter of the fluidized bed catalyst ranges from about 50 microns to about 200 microns.

8. The process for producing ethylene glycol according to claim 1, wherein the catalyst comprises from about 0.01 to about 20 parts by weight of the bismuth metallic element and an oxide thereof and from about 0.01 to about 20 parts by weight of the tungsten metallic element and an oxide thereof.

9. A process for producing ethylene glycol, the process comprising contacting an oxalate as a raw material with a fluidized bed catalyst under the following conditions: a reaction temperature of from about 170° C. to about 270° C., a weight space velocity of the oxalate of from about 0.2 h$^{-1}$ to about 7 h$^{-1}$, a hydrogen/ester molar ratio of from about 20:1 to about 200:1, a reaction pressure of from about 1.5 MPa to about 10 MPa, and a reaction temperature difference $\varDelta$T of from about 1° C. to about 15° C., to produce an effluent containing ethylene glycol,
   wherein said fluidized bed catalyst is a catalyst comprising copper and an oxide thereof, and
   wherein the catalyst comprises from about 0.01 to about 20 parts by weight of the cerium metallic element and an oxide thereof and from about 0.01 to about 20 parts by weight of the niobium metallic element and an oxide thereof.

10. The process for producing ethylene glycol according to claim 1, wherein the oxalate is selected from the group consisting of dimethyl oxalate, diethyl oxalate and mixtures thereof.

* * * * *